United States Patent
Krueger et al.

(10) Patent No.: US 6,444,203 B2
(45) Date of Patent: Sep. 3, 2002

(54) ADMINISTERING BACTERIA TO IMPROVE SLEEP

(75) Inventors: James M. Krueger, Pullman, WA (US); Michael J. Pabst, Germantown, TN (US); Chantal Cayuela, Paris; Marie-Christine Degivry, Le Plessis-Robinson, both of (FR); Donna Hartley, Arlington, TX (US)

(73) Assignee: Compagnie Gervais Danone, Paris (FR)

( * ) Notice: Subject to any disclaimer, the term of this patent is extended or adjusted under 35 U.S.C. 154(b) by 0 days.

(21) Appl. No.: 09/466,768

(22) Filed: Dec. 20, 1999

(51) Int. Cl.⁷ .............. A01N 63/02; C12N 1/20
(52) U.S. Cl. ............... 424/93.44; 435/252.9; 435/253.4; 435/854; 435/885; 424/93.45
(58) Field of Search ............ 424/93.45, 93.4, 424/93.44; 435/252.1, 252.9, 253.4, 854, 885; 514/923

(56) References Cited

U.S. PATENT DOCUMENTS

| | | | | |
|---|---|---|---|---|
| 4,110,476 A | * | 8/1978 | Rhodes | 426/41 |
| 4,624,853 A | * | 11/1986 | Rudin | 426/61 |
| 4,698,330 A | | 10/1987 | Krueger et al. | 514/19 |
| 4,837,036 A | * | 6/1989 | Baker et al. | 426/43 |
| 5,716,615 A | | 2/1998 | Cavaliere Vesely et al. | 424/93.4 |
| 5,759,598 A | * | 6/1998 | Gaier | 426/56 |

FOREIGN PATENT DOCUMENTS

| | | |
|---|---|---|
| CH | 654330 | 2/1986 |
| CN | 1114217 | 1/1996 |
| WO | WO 88/00438 | 1/1988 |
| WO | 96 11014 | 4/1996 |
| WO | WO 96/20607 | * 7/1996 |
| WO | 00 67696 | 11/2000 |

OTHER PUBLICATIONS

Dairy Markets Weekly, p. 8, "French Yoghurt Cure For Insomnia", Mar. 1997.*
Pabst et al., "Effects of Muramyl Peptides on Macrophages, Monokines, and Sleep," Neuroimmunomodulation, 1999; 6:261–283.
Johannsen et al., "Somnogenic Activity of Muramyl Peptide–Derived Immune Adjuvants," Int. J. Immunopharmac, 1994; vol. 16, No. 2:109–116.
Tannock. G.W., Probiotic properties of lactic–acid bacteria: plenty of scope for fundamental R&D, Trends in Biotechnology, GB, Elsevier Publications, Cambridge, vol. 15, No. 7 (1997).

* cited by examiner

*Primary Examiner*—David M. Naff
*Assistant Examiner*—Mike Meller
(74) *Attorney, Agent, or Firm*—Piper Rudnick LLP; Steven B. Kelber

(57) ABSTRACT

A method of improving sleep in a mammal having a sleep disorder is disclosed. The method includes identifying the mammal having a sleep disorder and then administering *Lactobacillus acidophilus* CNCM I-2274, *Lactobacillus acidophilus* CNCM I-2132, *Lactobacillus helveticus* CNCM I-2275, *Streptococcus thermophilus* CNCM I-1520, *Streptococcus thermophilus* CNCM I-2272 or mixtures thereof. The method increases the length of the non rapid eye movement sleep phase and decreases the length of the rapid eye movement sleep phase. The bacteria can be administered in an orally consumable food product or a dietary supplement.

7 Claims, 4 Drawing Sheets

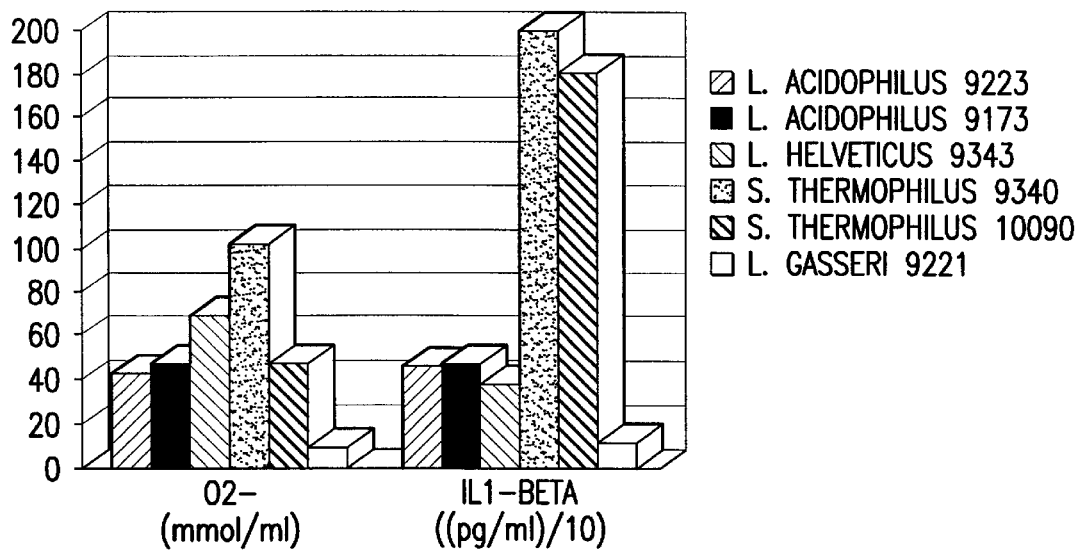

CONCENTRATION OF SUPEROXIDE UNION ($O_2$) AND IL-1$\beta$ MEASURED IN THE MONOCYTE CULTURE SUPERNATANT AFTER 18 TO 24 HR OF CONTACT BETWEEN MONOCYTES AND BACTERIAL CELLS. THESE RESULTS WERE OBTAINED WITH BACTERIAL SUSPENSIONS AT A CONCENTRATION OF 0.5 ng OF BACTERIAL PROTEIN/ml FOR THE PRODUCTION OF SUPEROXIDE, AND AT 50 ng BACTERIAL PROTIEN/ml FOR THE PRODUCTION OF IL-1$\beta$.

FIG.1

CORRELATION BETWEEN THE CONCENTRATIONS OF IL-1β AND OF TNFα MEASURED IN CULTURE SUPERNATANTS AFTER 16 HOURS OF CONTACT BETWEEN MONOCYTES AND BACTERIAL CELLS.
(RESULTS FROM INDEPENDENT EXPERIMENTS.)

PERCENT OF RECORDING TIME PASSED IN NREM PHASE AND IN REM PHASE AS A FUNCTION OF TIME (HRS) AFTER INJECTION OF 0.1 OR 1.0 mg/kg OF CELL WALLS OF *LACTOBACILLUS ACIDOPHILUS* 9223. (*$p<0.05$ BY STUDENT-NEWMAN-KEULS METHOD). ○ CONTROL; ● CELL WALLS.

PERCENT OF RECORDING TIME PASSED IN NREM PHASE AND IN REM PHASE AS A FUNCTION OF TIME (HRS) AFTER INJECTION OF 0.1 AND 1.0 mg/kg OF CELL WALLS OF *LACTOBACILLUS GASSERI* 9221. (*p<0.05 STUDENT-NEWMAN-KEULS METHOD). ○ CONTROL; ● CELL WALLS.

ADMINISTERING BACTERIA TO IMPROVE SLEEP

BACKGROUND OF THE INVENTION

1. Field of the Invention

The present invention concerns non-pathogenic lactic acid bacteria and food products containing the bacteria. The cell walls of these lactic acid bacteria are susceptible to the action of muramidase-type enzymes. The enzymes produce cell wall fragments called muramylpeptides that, when ingested, improve the quality of sleep.

2. State of the Art

Today many people have difficulty falling asleep or suffer from sleep disturbances such as insomnia. To reduce these problems, many pharmaceutical products containing benzodiazepines or barbiturates have been developed. However, these products should be administered under the care of a physician due to their secondary effects such as drug dependence, daytime sleepiness, memory loss, and interactions with other substances, notably alcohol.

Research on infectious diseases has shown that infection by pathogenic bacteria provokes at least three physiological responses in the infected subject: an immune response, fever, and modification of sleep. The mediators of these reactions in the host are components of the cell walls of the bacteria responsible for the infection, specifically muramylpeptides (and also lipopolysaccharides in gram-negative bacteria). Research has shown that the cell walls of pathogenic bacteria such as *Staphylococcus aureus* are hydrolyzed by macrophages to yield free muramylpeptides. (Johannsen L. et al., 1994).

To avoid the secondary effects of medicines containing benzodiazepines or barbiturates, U.S. Pat. No. 4,698,330 proposes to use compositions based on purified muramylpeptides that have somnogenic activity. Although the administration of these muramylpeptides leads to an increase of the deep sleep called Non Rapid Eye Movement (NREM) sleep, it also provokes an increase of body temperature, requiring the concomitant administration of antipyretic compounds.

Patent applications CH 654 330 A, CN 1 114 217 A and WO 8800438 A describe compositions containing bacteria, notably lactic acid bacteria, that improve sleep. However these documents do not reveal how lactic bacteria intervene in the improvement of sleep. The effect on sleep, as well as the other advantages claimed (more energy, better appetite and digestion, alleviation of rheumatism, etc.) of such compositions containing lactic acid bacteria are said to result from the specific balance of nutrients and micro-nutrients contained in the described compositions.

BRIEF DESCRIPTION OF THE DRAWINGS

Understanding of this invention may be amplified by reference to the figures herein, which are not required for an understanding of the invention.

FIG. 1 graphically displays the amount of superoxide anion and IL-1β measured in a monocyte culture supernatant after contact with bacterial suspensions according to the invention.

SUMMARY OF THE INVENTION

Figure 2:
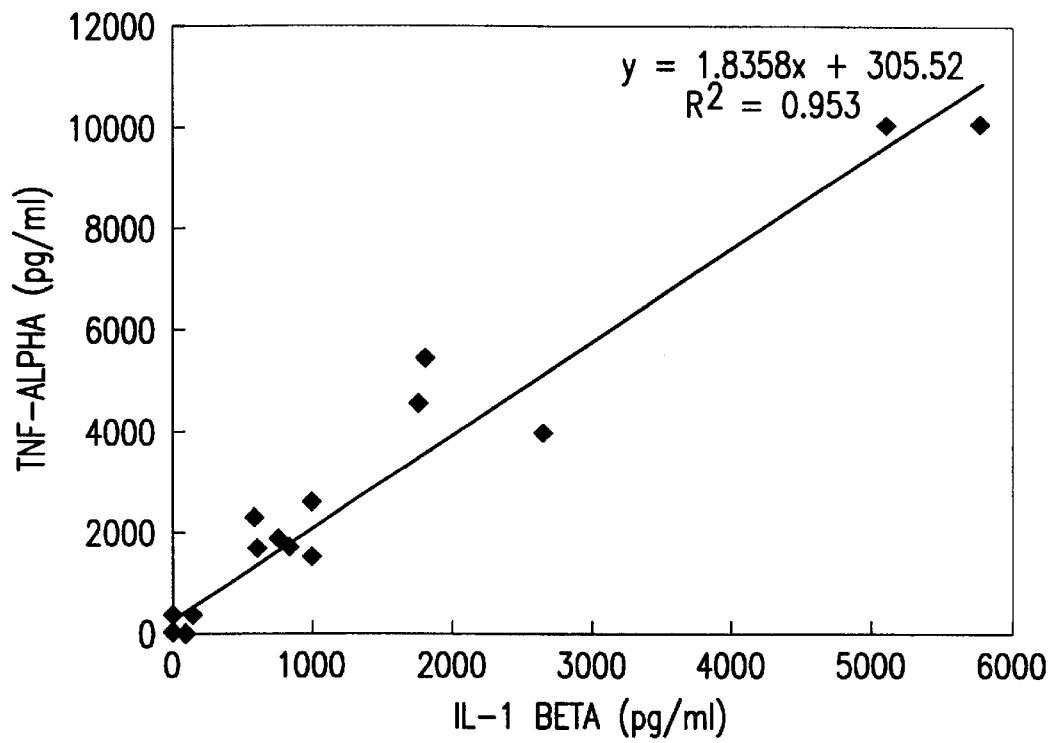
FIG. 2 is a graph demonstrating the correlation between concentrations of IL-1β and TNF α measured after exposure of monocytes to bacterial cells.

The inventors have found that non-pathogenic bacteria that do not cause an infection, such as lactic acid bacteria, can modify the phases of sleep, for example, can increase the length of NREM deep sleep. They noted that the lactic acid bacteria that lead to an increase the NREM phase are those whose cell wall is sensitive to the action of muramidase-type enzymes, such as lysozyme or mutanolysin.

The inventors studied the action of a muramidase, mutanolysin, on the cell walls of different lactic acid bacteria, in particular on the cell walls of *Lactobacillus gasseri* 9221 (CNCM I-2131), *Lactobacillus acidophilus* 9223 (CNCM I-2274), *Lactobacillus acidophilus* 9173 (CNCM I-2132), *Lactobacillus helveticus* 9343 (CNCM I-2275), *Streptococcus thermophilus* 9340 (CNCM I-1520) and *Streptococcus thermophilus* 10090 (CNCM I-2272). They noted that the cell walls of *Lactobacillus acidophilus* 9223 (CNCM I-2274), *Lactobacillus acidophilus* 9173 (CNCM I-2132), *Lactobacillus helveticus* 9343 (CNCM I-2275), *Streptococcus thermophilus* 9340 (CNCM I-1520) and *Streptococcus thermophilus* 10090 (CNCM I-2272) were hydrolyzed by the mutanolysin, yielding two fractions: a soluble fraction containing muramylpeptides and an insoluble fraction. In contrast, the cell walls of *Lactobacillus gasseri* 9221 (CNCM I-2131) were not hydrolyzed by mutanolysin, and muramylpeptides were not liberated. After incubating *Lactobacillus gasseri* 9221 (CNCM I-2131, deposited on Feb. 24, 1999) with mutanolysin, only the insoluble fraction could be recovered.

The effects of the lactic acid bacteria whose cell walls are hydrolyzed by muramidase-type enzymes on sleep has been validated by studying two experimental systems:

1) In vitro experiments with human monocytes showed that the lactic acid bacteria whose cell walls are hydrolyzed by mutanolysin to give a soluble fraction containing muramylpeptides were capable of strongly activating the monocytes, inducing increased production of superoxide anion, and also inducing production of the cytokines IL-1β and TNFα. Superoxide anion is an oxygen radical produced by monocytes that is directly involved in the killing of microbes. The cytokines are a family of protein inflammatory mediators that are known to be involved in the regulation of sleep. These monocyte activation effects were observed with both Lactobacillus and Streptococcus, including *Lactobacillus acidophilus* 9223, *Lactobacillus acidophilus* 9173, *Lactobacillus helveticus* 9343, *Streptococcus thermophilus* 9340 and *Streptococcus thermophilus* 10090.

2) In vivo experiments in rabbits showed that lactic acid bacteria whose cell wall is hydrolyzed by mutanolysin to give a soluble fraction containing muramylpeptides influenced the phases of sleep. Sleep was analyzed by electroencephalograms (EEG). Notably, such muramylpeptides increased the phase of sleep called NREM (Non Rapid Eye Movement) and decreased the phase of sleep called REM (Rapid Eye Movement).

The present invention describes several bacteria that improve the quality of sleep by increasing the length of the Non Rapid Eye Movement (NREM) sleep phase. Other important characteristics of the bacteria are that they are non-pathogenic for humans, and that their cell walls are sensitive to the action of muramidase-type enzymes, in particular to the action of mutanolysin.

DETAILED DESCRIPTION OF THE INVENTION

A lactic acid bacterium, as described in the invention, can be chosen from among the genera consisting of Lactobaccillus, Streptococcus, Lactococcus, and Bifidobacterium. The bacterium is preferably a lactic acid bacterium chosen from among the following:

*Lactobacillus acidophilus* 9223 (CNCM I-2274, deposited on Aug.. 3, 1999);

*Lactobacillus acidophilus* 9170 (CNCM I-2273, deposited on Aug. 3, 1999);

*Lactobacillus acidophilus* 9173 (CNCM I-2132, deposited on Feb. 24, 1999);

*Lactobacillus helveticus* 9343 (CNCM I-2275, deposited on Aug. 3, 1999);

*Streptococcus thermophilus* 9340 (CNCM I-1520, deposited on Dec. 30, 1994);

*Streptococcus thermophilus* 10090 (CNCM I-2272, deposited on Aug. 3, 1999).

Other strains are generally, publically available. CNCM I-2274, CNCM I-2273, CNCM I-2132, CNCM I-2275, CNCM I-1520, and CNCM I-2272 have been deposited with the Collection Nationale de Cultures de Microorganismes, Institut Pasteur, 28 rue du Docteur Roux, F-75724 Paris Cedex 15, France. These deposits were made pursuant to the Budapest Treaty conditions. All restrictions on access thereto will be withdrawn upon grant of a U.S. patent on this application.

The present invention also includes lactic acid bacteria cultures that associate two or more lactic acid bacteria strains, as described for a single strain in the invention.

The present invention also describes dietary supplements or foods containing lactic acid bacteria that improve the quality of sleep. The dietary supplements consist of a milk base, in particular a fermented milk, containing lactic acid bacteria strains whose cell walls are sensitive to the action of mutanolysin. The ingestion of such a dietary supplement or food will improve the quality of sleep.

Milk is chosen from among the milks of various animal species. The milk might be partially or completely skimmed. The milk base might involve products resulting from the dilution or the concentration of these milks, such as, for example, retentates of ultrafiltration or diafiltration. The milk base might involve media based on milk such as bases for milky foods or milk mixes for yogurt or fermented milks. These milks can be supplemented with lactose, minerals, vitamins, fats, water soluble milk solids, extracts of plants, flavorings, etc.

In an alternative approach, this dietary supplement or food can also be obtained from a plant substrate, such as from soy milk, juice or fruit pulp.

For example, a dietary supplement or food according to the invention, is obtained by putting in place the following process: A milk base is inoculated with at least one strain of a lactic acid bacterium containing $10^6$ to $10^7$ colony-forming units per ml. Conditions of incubation vary according to the strain or culture of lactic acid bacteria used. For example, if the culture is composed of a strain of *Streptococcus thermophilus* or a mixture containing at least one strain of *Streptococcus thermophilus*, the optimal culture conditions are 25 to 44° C. for 3 hr. to 24 hr. If the culture is composed of strains of *Lactobacillus acidophilus* or *Lactobacillus helveticus*, or a mixture containing at least a strain of *Lactobacillus acidophilus* or *Lactobacillus helveticus*, the optimal culture conditions are 37 to 44° C. for at least 8 hr. to 16 hr.

The milk base inoculated with a culture can be supplemented with peptide N3, yeast extract, antioxidants such as cysteine, vitamins, soluble fibers such as oligosaccharides or other substrates currently used to encourage the growth of the lactic acid bacteria strains used.

The lactic acid bacteria, or the dietary supplements that contain them, permit improved sleep quality by increasing the NREM phase and/or decreasing the REM phase. An increase of the NREM phase of sleep corresponds to an increase of deep sleep. An increase of the deep sleep phase leads to better recuperation from fatigue, greater alertness during the day, and other benefits.

Further, lactic acid bacteria, being non-pathogenic microorganisms, can be administered to improve the quality of sleep without the risk of triggering an excessive reaction of the immune system. Lactic acid bacteria interact positively with the immune system without inducing pathological reactions (like overproduction of cytokines) such as those reactions provoked by pathogenic bacteria.

In addition, the use of lactic acid bacteria to improve the quality of sleep does not provoke the secondary effects associated with taking barbiturates or benzodiazepines.

The present invention will be better understood with the help of the additional information that follows which provides non-restrictive examples illustrating the properties of lactic acid bacteria strains according to the invention.

In Vitro Experiments

Hydrolysis of the Different Lactic Acid Bacteria Cell Walls by Mutanolysin

Cell walls were prepared from lactic acid bacteria cultures in stationary phase. The bacterial cells were broken in a French press. This preparation was treated with sodium dodecyl sulfate detergent and with trypsin to obtain a crude extract of deproteinated cell walls. The cell wall peptidoglycan from the lactic acid bacteria was then digested with mutanolysin from *Streptomyces globisporus* (Sigma-Aldrich, St. Louis, Mo.). Peptidoglycan (5–10 mg/ml) was incubated with 0.1 to 0.25 mg of mutanolysin at 37° C. in phosphate buffer, pH 5.8, for 24 hours. The resulting hydrolysate was separated by centrifugation, using centrifugal concentrators (Pall Filtron Microsep™, Northborough, Mass.) and a membrane with a cutoff of 10kDa to separate the low molecular weight molecules from the remaining higher molecular weight material.

The bacteria tested were *Lactobacillus gasseri* 9221, *Lactobacillus acidophilus* 9223, *Lactobacillus acidophilus* 9173, *Lactobacillus helveticus* 9343, *Streptococcus thermophilus* 9340 and *Streptococcus thermophilus* 10090.

The cell walls of five of the bacteria tested were partially hydrolyzed by mutanolysin, allowing the recovery of a soluble fraction containing muramylpeptides and an insoluble fraction resistant to the action of mutanolysin.

Only the cell walls of *Lactobacillus gasseri* 9221 (CNCM I-2131, deposited on Feb. 24, 1999) was not hydrolyzed by mutanolysin and did not liberate muramylpeptides.

Induction by Lactic Acid Bacteria of the Production of Superoxide Anion and Cytokines in Human Monocytes Monocytes were isolated from healthy human adults. Erythrocytes were sedimented with high molecular weight dextran. Mononuclear cells were separated from neutrophils by Histopaque gradient (Sigma-Aldrich). Mononuclear cells, which contained both monocytes and lymphocytes, were cultivated at a density of $1.5 \times 10^6$ cells/ml, which corresponds to approximately $0.5 \times 10^6$ monocytes/ml, in a modified Earle's salt solution medium, in an incubator at 37° C., with 5% $CO_2$. In the experiments designed to measure the production of TNF α by monocytes, the monocytes were cultivated in presence of 0.2% heat-inactivated (56° C., 30 min.) Type AB human serum.

The bacteria tested were *Lactobacillus gasseri* 9221, *Lactobacillus acidophilus* 9223, *Lactobacillus acidophilus* 9173, *Lactobacillus helveticus* 9343, *Streptococcus thermophilus* 9340 and *Streptococcus thermophilus* 10090. The pellets of lactic acid bacteria were put in suspension to obtain a concentration of bacterial proteins of 1 mg/ml (determined by the Lowry protein assay). Diluted suspensions containing from 0.1 to 300 ng/ml of bacterial proteins were tested.

The production of superoxide anion ($O_2$) by monocytes was measured by the cytochrome c method, after having activated the monocytes with phorbol myristate acetate (PMA) for 40 min at 37° C. in an incubator with 5% $CO_2$. The reduction of cytochrome by the superoxide anion was measured spectrophotometrically at 550 nm. The extinction coefficient of 0.021 $\mu M^{-1}$ was used to calculate the quantity of superoxide anion produced.

Cytokine production was measured by ELISA (Enzyme Link Immunosorbent Assay) on samples of the monocyte culture medium. ELISA kits for IL-1β(BioSource International, Carmarillo, Calif.) and TNFα (Genzyme Diagnostics, Cambridge, Mass.) were used.

FIG. 1 shows that *Lactobacillus acidophilus* 9223, *Lactobacillus acidophilus* 9173, *Lactobacillus helveticus* 9343, *Streptococcus thermophilus* 9340, and *Streptococcus thermophilus* 10090 were capable of strongly activating human monocytes to induce production of superoxide anion and IL-1β. In contrast, *Lactobacillus gasseri* 9221, whose cell wall is insensitive to the action of mutanolysin, induced only a weak activity in human monocytes. FIG. 2 shows that the production of IL-1β and TNFα were closely correlated ($R^2=0.95$).

In Vivo Experiments
Sleep Improving Activity of Lactic Acid Bacteria Cell Walls in Rabbits Sleep experiments were done with rabbits using one of the lactic acid bacteria strains, *Lactobacillus acidophilus* 9223, that gave a positive response in the in vitro test, and one strain, *Lactobacillus gasseri* 9221, that was negative in the in vitro test. Cell walls of the bacteria tested were administered by intravenous injection.

The test animals were adult male New Zealand white rabbits (Myrtle Rabbitery, Thompson Station, Ten.) weighing between 3.5 and 4.5 kg.

The rabbits were operated on to implant a system of recording of their electroencephalograms (EEG). The system allowed animals to move without constraint. On separate days, each animal received either the vehicle or one of the substances to be tested. Therefore, each animal served as its own control. The marginal ear vein was used for the intravenous injection. The volume of injection was 0.1 ml/kg.

The recordings were interpreted and classified according to three states of wakefulness: awakening phase, NREM phase (low frequency electroencephalogram, high amplitude electroencephalogram, and no body movement which characterizes deep, heavy sleep), and REM phase (high frequency electroencephalogram, low amplitude electroencephalogram, and occasional body movements that characterize paradoxal sleep). The length of every phase was expressed as a percentage in the recorded time per hour.

Figure 3:
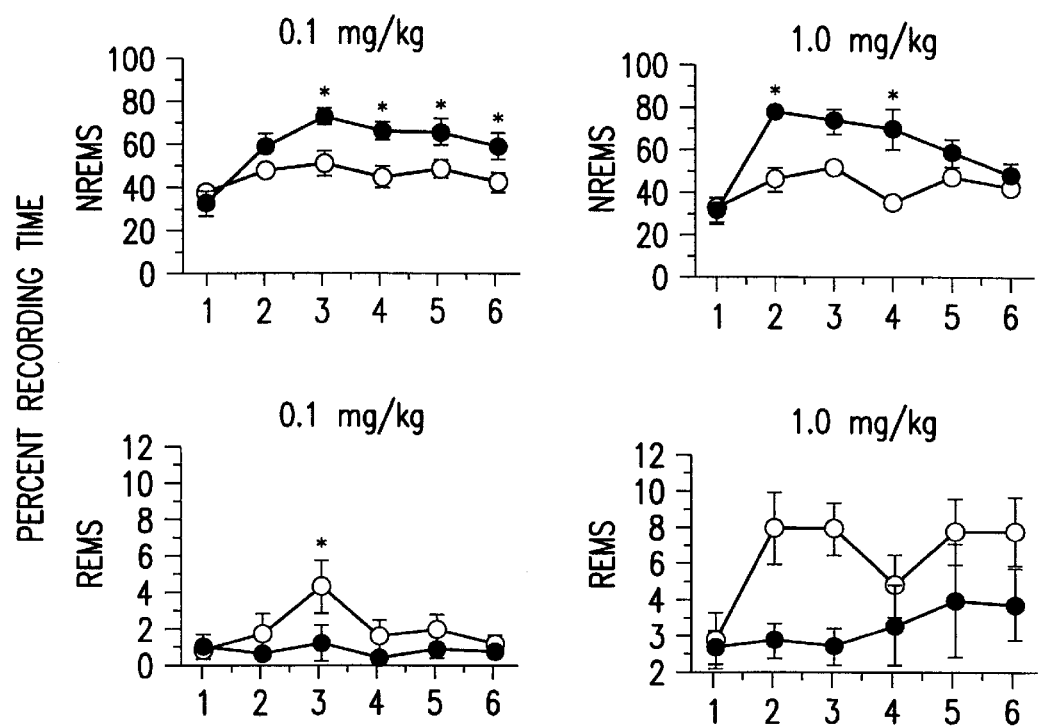
FIG. 3 reflects a graphic representation of the percent of time spent in NREM phase and REM phase, as a function of hours, after injection of two different levels of concentration of cell wall material according to the invention.
Figure 4:
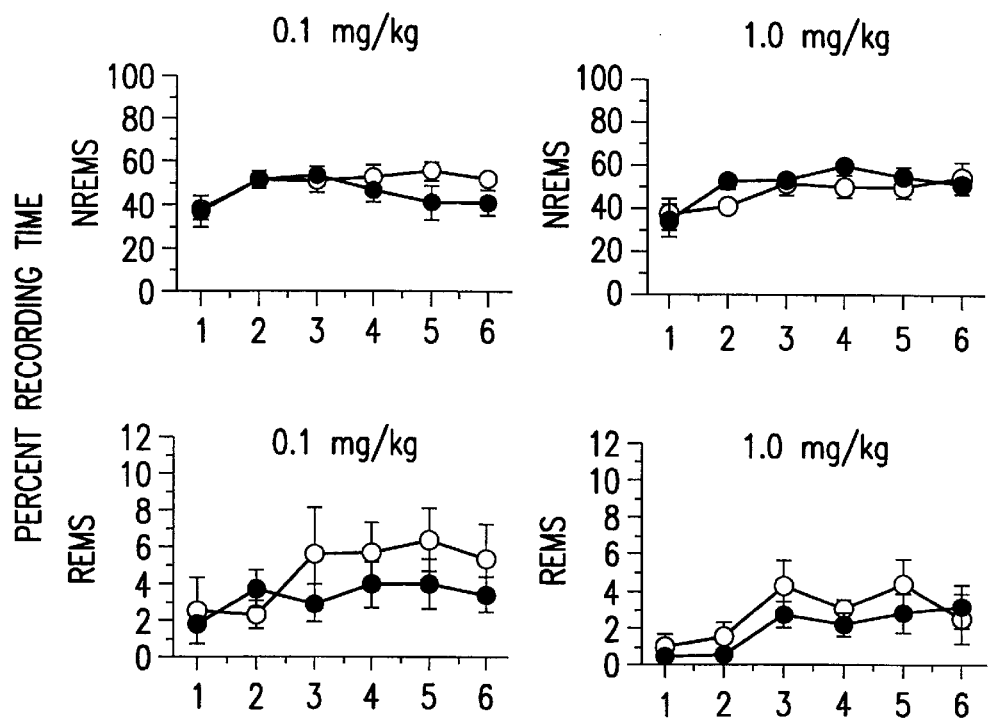
FIG. 4 presents a graphic representation similar to that of FIG. 3, wherein the bacterial cell wall material is not susceptible to digestion by muramidase-type enzymes to provide a soluble fraction containing muramylpeptides.

FIG. 3 shows that the cell walls of *Lactobacillus acidophilus* 9223 administered at doses of 0.1 mg/kg and 1.0 mg/kg influenced sleep by increasing the NREM phase and by decreasing the REM phase. The increase of the NREM phase started during the second hour after injection and persisted throughout the test. In contrast, FIG. 4 shows that the cell walls of *Lactobacillus gasseri* 9221 did not have a significant effect on sleep.

Therapeutic Administration

The subject matter of this invention is effectively administered to mammals, including humans, orally. Effective amounts will vary dramatically, depending on the individual, the state or condition of the individual, the desired result, etc. Oral administration is effective to mammals, including humans, because digestion of the lactic acid bacterial cell walls by muramidase-type enzymes naturally occurs throughout the digestive tract, beginning in the oral cavity, and continuing through the stomach and intestines. Alternatively, pre-digested muramylpeptides may be administered orally, by injection, or by suppository. The injection may be either IV or IM. Preferably, for ease of administration and for patient comfort, administration is by an oral route.

The active agent, muramylpeptides, are water soluble. Lactic acid bacteria, if administered as such, may be provided in any pharmaceutically acceptable carrier, and are preferably provided as an element or additive to a food product, preferably including milk or fermented milk products. In one preferred embodiment, the lactic acid bacteria or predigested muramylpeptides are provided in a yogurt product. The yogurt may be flavored or unflavored, and the nature of the yogurt itself, save for the active agent provided herein, does not constitute an aspect of the invention. Lactic acid bacteria are advantageously orally administered in an amount ranging from 1 milligram–1 gram/kilogram of body weight per day. Sleep improvement is a complicated mechanism, and the condition of the subject being treated will enormously impact the effective dosage. The vehicle for administration, if the administration is oral, is substantially unlimited provided it does not contain muramylpeptide-digesting enzymes, or otherwise does not block the activity of the active agent of this invention in stimulating superoxide anion production by monocytes, as well as cytokine production.

As another method of determining effective amounts, an effective dosage of a 1 mg/ml lactic acid bacteria protein suspension will range from between 0.01–100 ml/kg.

This invention has been described generically, and by reference to specific embodiments. Examples are not intended to be, and should not be construed as limiting, unless specifically so indicated. Alternatives will occur to those of ordinary skill in the art, particularly with respect to the identification of non-pathogenic lactic acid bacteria, vehicle or carrier, concentration or suspension, or other aspects of preparation. These alternatives remain within the scope of the invention, unless excluded by the recitation of the claims set forth below.

What is claimed is:

1. A method of improving sleep in a mammal having a sleep disorder comprising the steps of:

identifying a mammal with said sleep disorder; and administering a bacteria selected from the group consisting of *Lactobacillus acidophilus* CNCM I-2274, *Lactobacillus acidophilus* CNCM I-2132, *Lactobacillus helveticus* CNCM I-2275, *Streptococcus thermophilus* CNCM I-1520, *Streptococcus thermophilus* CNCM I-2272, and mixtures thereof;

wherein length of non rapid eye movement sleep phase is increased or length of rapid eye movement sleep phase is decreased in said mammal.

2. The method of claim 1, wherein the amount of bacteria administered is in an amount ranging from 1 milligram to 1 gram/kg of body weight per day.

3. The method of claim 1, wherein said bacteria is administered to said mammal in the form of an orally consumable food product or a dietary supplement.

4. The method of claim 3, wherein said food product is a milk product.

5. The method of claim 4, wherein said milk product is a fermented milk product.

6. The method of claim 5, wherein said milk product is a yogurt.

7. The method of claim 1, wherein said mammal is a human.

\* \* \* \* \*